(12) United States Patent
Schwaneberg

(10) Patent No.: US 7,790,374 B2
(45) Date of Patent: Sep. 7, 2010

(54) PROCESS FOR SEQUENCE SATURATION MUTAGENESIS (SESAM)

(75) Inventor: Ulrich Schwaneberg, Bremen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 164 days.

(21) Appl. No.: 10/573,639

(22) PCT Filed: Sep. 30, 2004

(86) PCT No.: PCT/EP2004/010911

§ 371 (c)(1),
(2), (4) Date: Mar. 28, 2006

(87) PCT Pub. No.: WO2005/035757

PCT Pub. Date: Apr. 21, 2005

(65) Prior Publication Data

US 2006/0223148 A1    Oct. 5, 2006

(30) Foreign Application Priority Data

Oct. 2, 2003    (EP)    ................................. 03022311

(51) Int. Cl.
C12Q 1/68    (2006.01)
C12P 19/34    (2006.01)
(52) U.S. Cl. ......................................... 435/6; 435/91.2
(58) Field of Classification Search ........................ None
See application file for complete search history.

(56) References Cited

U.S. PATENT DOCUMENTS 6,238,884 B1 *   5/2001   Short et al. ..................... 506/1
6,239,159 B1 *   5/2001   Brown et al. ................. 514/394
6,428,955 B1 *   8/2002   Koster et al. .................... 435/6
6,713,294 B1 *   3/2004   Krokan et al. ............... 435/195

FOREIGN PATENT DOCUMENTS

WO    WO 03/050305    6/2003

OTHER PUBLICATIONS

Henikoff (1990) Nucl. Acid Res. vol. 18 No. 10 pp. 2961-2966.*
Cosstick and Vyle (1990) Nucl. Acids Res. vol. 18 No. 4 pp. 829-835.*
Lutz et al (2001) Nucl. Acids Res. vol. 29 No. 4 e16.*
Xu, H. et al., "Random Mutagenesis Libraries: Optimization and Simplification by PCR", BioTechniques, 1999, vol. 27, No. 6, pp. 1102-1108.
Zaccolo, M. et al., "An Approach to Random Mutagenesis of DNA Using Mixtures of Triphosphate Derivatives of Nucleoside Analogues", J. Mol. Biol., 1996, vol. 255, pp. 589-603.
Arnold, F. H. et al., "How Enzymes Adapt: Lessons from Directed Evolution", Trends in Biochem. Sci., 2001, vol. 26, No. 2, pp. 100-106.
Cadwell, R. C. et al., "Randomization of Genes by PCR Mutagenesis", PCR Meth. Appl., 1992, vol. 2, pp. 28-33.
Cadwell, R. C. et al., "Mutagenic PCR", PCR Meth. App., 1994, vol. 3, pp. S136-S140.
Kuipers, O. P., "Random Mutagenesis by Using Mixtures of dNTP and dITP in PCR", Meth. Mol. Biol., 1996, vol. 57, pp. 351-356.
Lin-Goerke, J. L. et al., "PCR-Based Random Mutagenesis Using Manganese and Reduced dNTP Concentration", BioTechniques, 1997, vol. 23, pp. 409-412.
"Recombinant DNA", in Methods in Enzymology, Part F, Wu R., Editor, Academic Press Inc., 1987, vol. 55, pp. 555-569.

* cited by examiner

*Primary Examiner*—Kenneth R. Horlick
*Assistant Examiner*—David C Thomas
(74) *Attorney, Agent, or Firm*—Connolly Bove Lodge & Hutz, LLP

(57) ABSTRACT

A process for the mutagenesis of a double-stranded polynucleotide sequence (master sequence) of n base-pairs having a (+)-strand and a complementary (−)-strand comprising the steps (i) creation of a collection of single-stranded fragments of the (+)-strand of the master sequence wherein all members of the collection have the same 5'-terminus and have a deletion in the 3-terminus such that the collection represents (+)-strands with a length of n−1, n−2, n−3, . . . nucleotides; (ii) introduction of at least one universal or degenerate nucleotide at the 3'-terminus of the (+) strand produced in step (i); (iii) elongation of the (+)-strand produced in step (ii) to the full length of the master sequence using the (−)-strand or fragments thereof as a template strand for the elongation; (iv) synthesis of a (−)-strand by using the (+)-strand produced in step (iii) as a template strand thereby effecting mutations in the (−)-strand at the positions of the previous universal or degenerate nucleotides compared to the master sequence.

15 Claims, 6 Drawing Sheets

SEQUENCE LISTING

```
<160> NUMBER OF SEQ ID NOS: 2

<210> SEQ ID NO 1
<211> LENGTH: 25
<212> TYPE: DNA
<213> ORGANISM: Unknown
<220> FEATURE:
<223> OTHER INFORMATION: Reverse primer

<400> SEQUENCE: 1
gaccggcgct cagttggaat tctag                                       25

<210> SEQ ID NO 2
<211> LENGTH: 23
<212> TYPE: DNA
<213> ORGANISM: Unknown
<220> FEATURE:
<223> OTHER INFORMATION: Forward primer

<400> SEQUENCE: 2
gaccatgatt acgccaagct tgc                                         23
```

PROCESS FOR SEQUENCE SATURATION MUTAGENESIS (SESAM)

RELATED APPLICATIONS

This application is a national stage application (under 35 U.S.C. 371) of PCT/EP2004/010911 filed Sep. 30, 2004 which claims benefit to European application 03022311.9 filed Oct. 2, 2003.

Inspired by Darwinian evolution in nature, random mutagenesis methods have been developed for tailoring proteins to our needs and elucidating structure-function relationships (1). Creating diversity on the genetic level is the complementary tool to gene shuffling since it creates the opportunity to introduce novel mutations for adapting proteins to non-natural environments in biotechnological processes. The sequence space of a truly randomized library is, by its nature, not limited by a pre-selection for function under physiological conditions. Parental genes used in gene shuffling experiments are optimized by natural evolution for function under physiological conditions.

Among random mutagenesis methods, error-prone PCR methods based on inaccurate amplification of genes are most commonly used due to their simplicity and versatility. Error-prone PCR methods can be divided into three categories: A) Methods that reduce the fidelity of the polymerase by unbalancing nucleotides concentration and/or adding of manganese chloride (2-4), B) Methods that employ nucleotide analogs (5,6), and C) Combined methods (A and B; (7)).

SPECIFICATION

The invention relates to a process for the mutagenesis of a double-stranded polynucleotide sequence (master sequence) of n base-pairs having a (+)-strand and a complementary (−)-strand comprising the steps
(i) creation of a collection of single-stranded fragments of the (+)-strand of the master sequence wherein all members of the collection have the same 5'-terminus and have a deletion in the 3'-terminus such that the collection represents (+)-strands with a length of n−1, n−2, n−3, . . . nucleotides;
(ii) introduction of at least one universal nucleotide or degenerate nucleotide at the 3'-terminus of the (+) strand produced in step (i);
(iii) elongation of the (+)-strand produced in step (ii) to the full length of the master sequence using the (−)-strand or fragments thereof as a template strand for the elongation;
(iv) synthesis of a (−)-strand by using the (+)-strand produced in step (iii) as a template strand thereby effecting mutations in the (−)-strand at the positions of the previous universal nucleotides or degenerate nucleotides compared to the master sequence.

A universal nucleotide is a nucleotide that can pair to all four standard nucleotides. For example deoxyinosinetriphosphate (dITP) when incorporated into a polynucleotide strand allows base pairing with Adenine, Guanine, Thymine and Cytosine.

Preferred universal nucleotides are deoxyinosine, 3-nitropyrrole and 5-ntroindole.

A degenerate nucleotide is a nucleotide that can pair to less than all four standard nucleotides. Preferred degenerate nucleotides are $N^6$-methoxy-2,6-diaminopurine (K), $N^6$-methoxy-aminopurine (Z), hydroxylaminopurine (HAP), 2'-deoxyribonucleoside triphosphate (dyTP), 6H,8H-3,4-dihydropyrimidol [4,5-c][1,2]oxazin-7-one (P), $N^4$-aminocytidine, $N^4$-hydroxy-2'-deoxycytidine, $N^4$-methoxy-2'-deoxycytidine and 8-oxodeoxyguanosine triphosphate (8-oxo-G).

A nucleotide analog with promiscuous base pairing property means that a nucleotide that is based on a purine or pyrimidine structure (e.g. A, G, C, T) which is modified in one or more of its functional groups, can have base pairs to more than one other nucleotides, e.g. to two, three or four nucleotides. Also the universal nucleotides and degenerate nucleotides are embraced by the term nucleotide analog with promiscuous base pairing property.

A preferred embodiment of the invention is a process as described above, wherein an oligonucleotide of the general formula

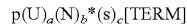

with
p=5'-phosphate or hydroxy-group or any chemical group capable of forming diester bonds
U=universal or degenerate bases
a=arbitrary integral number from 0 to 10000, preferred from 1-100
N=mixture of four bases (A/T/G/C (standard nucleotides)
b=arbitrary integral number from 0 to 100, preferred from 1-10,
*=cleavable group such as phosphothioate bonds in phosphothioate nucleotides
S=standard nucleotide or nucleotide analog
c=arbitrary integral number from 0 to 100, preferred from 1-10,
[TERM]=a dye terminator or any group preventing elongation of the oligonucleotide, with the proviso that a+b>0, preferred >1, more preferred >2, is used in step (ii) to introduce universal or degenerate bases to the collection of single-stranded fragments created in step (i).

[TERM] can be any group which prevents the elongation of the above-mentioned oligonucleotide, preferably an hydrogen or a dye terminator. Preferred dye terminators are Coumarin, 6-FAM, Fluorescein, Fluorescein-dT, JOE, Oregon Green, ROX, TAMRA or Texas Red-X.

Another preferred embodiment of the invention is the creation of a collection of single-stranded fragments of the (+)-strand of the master sequence according to step (i) by incorporating alpha-phosphothioate nucleotides, preferably dATPαS, dGTPαS, dTTPαS, dCTPαS, into the PCR products and subsequent cleavage of the phosphothioate bond by iodine under alkaline conditions.

Another preferred embodiment of the process according to the invention is the following process for step (iii): Starting from a double-stranded plasmid which harbors the master sequence a (−) single stranded plasmid polynucleotide sequence is synthesized using a primer which anneals downstream of the (+)-strand of the master sequence. This (−) single stranded plasmid polynucleotide sequence is annealed with the (+)-strands produced in step (ii). The (+)-strands are elongated to the full length of the master sequence using the (−)-strand as a template. This process is shown in FIG. 3.

Further preferred embodiments are disclosed in the claims.

Step (i): Creating DNA Fragment Pool with Length Distribution

In the first step, PCR is performed using biotinylated forward primer and non-biotinylated reverse primer in the presence of both standard nucleotides and α-phosphothioate nucleotides. α-Phosphothioate nucleotides are similar to normal nucleotides, except that an oxygen atom of α-phosphate is replaced by a sulphur atom. Phosphothioate bond is susceptible to iodine cleavage in alkaline condition. Due to random distribution of phosphothioates in the DNA, a library of fragments that stop at every single base is generated in a single PCR. Nicks may form if the binding between two complementary strands is strong. Biotinylated fragments are isolated using Strepavidin-coated biomagnetic beads. DNA melting solution (0.1 M NaOH) is then used to remove non-biotinylated strands and undesired fragments. Biotinylated fragments can easily be released from biomagnetic beads by boiling in 0.1% SDS solution. A scheme of the first step is shown in FIG. 1a and the corresponding experimental data is shown in FIG. 1b.

Step (ii): Enzymatic Elongation

To elongate DNA fragments with universal bases or degenerate bases (FIG. 2), two approaches can be used. In a first approach terminal deoxynucleotidyl transferase has been used for incorporating ambiguous bases (universal base or degenerate base) at the 3'-termini. The second approach requires single-stranded DNA ligation between DNA fragments and a "special" oligo. This "special" oligo is 5'-phosphorylated to facilitate ligation. It is terminated with fluorescein to avoid intra- and intermolecular ligation and to quantify the incorporation. There are 3 distinct parts in this oligo: 1) "Mutational part" containing universal bases or degenerate bases, 2) "Adhesive part" consisting of three bases that encompasses all 64 possibilities by using equimolar of A/T/G/C in oligo synthesis. This part is designed to assist annealing in the subsequent PCR used for the full length gene synthesis. The "Redundant part" is connected to "Adhesive part" via phosphothioate bond that allows its cleavage by the iodine method. ssDNA ligation can be accomplished using ThermoPhage RNA Ligase II (Prokaria). ThermoPhage RNA Ligase 11 catalyses the ATP-dependent intra- and intermolecular formation of phosphodiester bonds between 5'-phopsphate and 3'-hydroxyl termini of single-stranded DNA or RNA. This enzyme is derived from thermophilic phage TS2126 that infects the thermophilic eubacterium *Thermus scotoductus*. This thermostable enzyme is homologous to RNA ligase derived from bacteriophage T4. It shows superior efficiency in ssDNA ligation as compared to T4 RNA ligase. The ligation efficiency was determined by ligating a fluorescein labelled oligo to single stranded DNA template. After the ligation, the 'Redundant part' is removed by iodine cleavage in alkaline condition.

Step (iii): Full-Length Gene Synthesis

The third step is extending the elongated fragments to full-length (FIG. 3). Here, we use a single-stranded template to avoid the wild-type amplification. Single-stranded template is synthesized using reverse primer. Methylated and hemimethylated parental genes are removed by Dpn I digestion. This procedure is similar to QuikChange Site-Directed Mutagenesis (Stratagene) except that only one non-mutagenic primer is used instead of a pair of mutagenic primers. Elongated fragments anneal to single-stranded template due to complementarities and extend the single strand to full-length. Reverse primers present in this PCR reaction can only anneal to the newly synthesized full-length single strand and not to single-stranded template. After reverse primer binding the double stranded full-length genes will be synthesized. Double-stranded DNAs will contain nucleotide analogs in one strand and standard nucleotides in another strand.

In the event where a double-stranded template is used in this PCR instead of a single-stranded one we would observe that the reverse primer binds to its complementary template strand, amplifying double stranded DNA that do not contain nucleotide analogs.

Step (iv): Nucleotide Replacement

In the last PCR the nucleotide analog-containing strands are used as templates to replace nucleotide analogs with standard nucleotides (FIG. 4). After restrictive digestion, mutated genes are cloned into suitable expression vector, transformed and expressed in *E. coli*. Randomly selected clones were picked and grown in small cultivation tubes (5 ml; $LB_{amp}$). Isolated plasmid DNA is subsequently sequenced. Preliminary sequencing results with 100 clones proved the proper replacement and showed a bias as expected for inosine (FIG. 5 and FIG. 6).

Generation of mutant libraries using the SeSaM method can be completed within 1-2 days. The SeSaM method offers the following advantages:

1) Able to saturate every single position of a sequence with all 20 possible naturally occurring amino acids.
2) No bias in mutational spectra if truly universal bases are used.
3) Mutation spectra can be manipulated using transition-favoured or transversion-favoured degenerate bases.
4) Controllable length of mutation regions by designing proper special oligos.
5) Fragment size distribution can be controlled by using Sp-dATPαS/Sp-dTTPαS/Sp-dGTPαS/Sp-dCTPαS or combination of them.

Materials and Methods

All chemicals used were of analytical-reagent grade or higher quality and were purchased from Sigma-Aldrich Chemie GmbH (Taufkirchen, Germany), Applichem GmbH (Darmstadt, Germany) or Carl Roth GmbH+Co (Karlsruhe, Germany). pEGFP plasmid was purchased from BD Biosciences (Heidelberg, Germany).

A thermocycler (Mastercycler gradient; Eppendorf, Hamburg, Germany) and thin-wall PCR tubes (Multi-Ultra tubes; 0.2 ml; Carl Roth GmbH+Co., Karlsruhe, Germany) were used in all PCRs. The reaction volume of all PCRs was always 50 µl.

(Preparatory Step 1) Single-Stranded pEGFP Preparation:

For each PCR, 5 U Pfu Turbo polymerase (Stratagene, Amsterdam, Netherlands), 0.2 mM dNTP mix (New England Biolab, Frankfurt, Germany), 12.6 pmol reverse primer (5'-GACCGGCGCTCAGTTGGAATTCTAG-3', SEQ ID NO: 1) and 48.6-54.3 ng plasmid pEGFP (Miniprep, Qiagen, Hilden, Germany) were used. After PCR (95° C. for 30 sec 1 cycle, 95° C. for 30 sec/55° C. for 1 min/68° C. for 4 min 40 cycles), 40 U of Dpn I was added followed by incubation at 37° C. for 3 hours. Product recovery was done using a NucleoSpin Extract (Macherey-Nagel, Düren, Germany; elution volume of 35 µl for 200 µl PCR product).

(Preparatory Step 2) Cloning Vector Preparation:

24.3-27.1 µg plasmid pEGFP (Miniprep; QIAGEN) was first digested with 30 U EcoRI (New England Biolab) in a reaction mixture of 100 µl. The reaction mixture was incubated at 37° C. for 3 hours. The linearized plasmid was purified with NucleoSpin Extract (Machery-Nagel; Elution volume of 50 µl for 100 µl reaction mixture). 4.9-5.6 µg of linearized plasmid pEGFP was subjected to second digestion with 20 U Age I (New England Biolab) in a reaction volume of 50 µl. After incubation at 37° C. for 3 hours, the double digested plasmid was purified with NucleoSpin Extract (Macherey-Nagel; elution volume of 35 µl for 50 µl reaction mixture). Double digested pEGFP was used for subsequent cloning.

(Step 1) PCR with dATPαS:

For each PCR (94° C. for 3 min 1 cycle, 94° C. for 1 min/59.5° C. for 1 min/72° C. for 75 sec 31 cycles, 72° C. for 10 min 1 cycle), 2.5 U Taq DNA polymerase (Qiagen), 0.2 mM dNTP mix (New England Biolab), 0.2 mM Sp-dATPαS (Biolog Life Science Institute, Bremen, Germany), 12.6 pmol 5'-biotinylated forward primer (5'-GACCATGATTACGC-CAAGCTTGC-3', SEQ ID NO: 2), 12.6 pmol reverse primer (5'-GAC CGGCGCTCAGTTGGAATTCTAG-3', SEQ ID NO: 1) and 242.9-271.4 ng plasmid pEGFP (Miniprep; Qiagen) were used.

(Step 2) Iodine Cleavage of Thiophosphodiester Backbone:

The phosphothiate bond was cleaved with iodine (dissolved in ethanol; final concentration in the PCR tube 2 μM). The mixture was incubated at room temperature for 1 hour.

(Step 3) Preparation of Single Stranded DNA Fragments with Different Length:

Biotinylated DNA fragments from the forward primer were isolated using Dynabeads MyOne Streptavidin (DYNAL Biotech, Oslo, Norway) at room temperature. 50 μl of biomagnetic beads (10 mg/ml) were washed twice using 100 μl 2× B&W buffer (10 mM Tris-HCl, pH 7.5; 1.0 mM EDTA, 2.0 M NaCl). Washed biomagnetic beads were resuspended in 100 μl 2× B&W buffer and 100 μl of cleaved PCR product was added. After incubating for 20 min, the biotinylated DNA fragments were immobilized on the biomagnetic beads and the iodine was removed by washing with 100 μl 2× B&W buffer. Non-biotinylated DNA fragments were released after incubating in 100 μl DNA melting solution (0.1 M NaOH) at 37° C. for 10 min followed by bead washing steps with 100 μl of DNA melting solution and 100 μl 1× B&W buffer. The washed Dynabeads were boiled in 60 μl 0.1% SDS for releasing the DNA fragments from the solid support. The supernatant containing the DNA fragments was transferred to another tube immediately.

(Step 4) SDS Salt Removal from Eluted Single Stranded DNA Fragments:

Desalting was done using NucleoTrap kit (Macherey-Nagel, Duren, Germany). 400 μl of buffer NT2 was added to 100 μl of eluted DNA followed by 15 μl of NucleoTrap suspension. The mixture was incubated at room temperature for 10 min and gently shaked every 2-3 min. The sample was then centrifuged at 10000 g for 30 sec and after discarding the supernatant, the beads were washed with 500 μl of buffer NT3. The latter step was repeated once. The pellet was air-dried for 15 min at 37° C. to remove residual ethanol, resuspended in 55 μl Tris/HCl buffer (5 mM; pH 8.5) and incubated for DNA elution at 50° C. for 5 min for DNA elution. The suspension was pipetted into NucleoSpin Microfilter and centrifuged at 10000 g for 30 sec to separate beads from DNA containing solution.

(Step 5) Enzymatic Elongation of DNA Fragments with Universal Base:

Total reaction volume for each elongation reaction was 50 μl. In each reaction, 5 U terminal transferase (New England Biolabs), 0.25 mM CoCl$_2$, 0.4 μM dITP (Amersham Biosciences Europe GmbH, Freiburg, Germany), and 18 μl desalted DNA from step 4 were used. After incorporation of universal bases in the elongation reaction (37° C. for 30 min and heat deactivation of the transferase at 70° C. for 10 min), the product was purified following the QIAquick Nucleotide Removal Kit (QIAGEN; elution volume of 25 μl for 50 μl reaction mixture) protocol.

(Step 6) Full-Length Gene Synthesis:

For each PCR (94° C. for 3 min 1 cycle, 94° C. for 1 min/59.5° C.+0.2° C. (0.2° C. increment for each cycle) for 1 min/72° C. for 3 min 30 cycles, 72° C. for 10 min 1 cycle), 2.5 U Taq DNA polymerase (Qiagen), 0.2 mM dNTP mix (New England Biolab), 13.3 μl elongated DNA fragment, 20 pmol reverse primer (5'-GAC CGGCGCTCAGTTGGAAT-TCTAG-3', SEQ ID NO: 1) and 0.66-0.76 μg single-stranded reverse template (preparatory step 1) were used. After synthesizing the full-length gene a purification step was performed using the NucleoSpin Extract (Macherey-Nagel; elution volume of 35 μl for 150 μl PCR product).

(Step 7) Universal Base Replacement:

For each PCR (94° C. for 3 min 1 cycle, 94° C. for 1 min/52.7° C. for 1 min/72° C. for 75 sec 30 cycles, 72° C. for 10 min 1 cycle), 2.5 U Taq DNA polymerase (Qiagen), 0.2 mM dNTP mix (New England Biolabs), 20 pmol forward primer (5'-GACCATGATTACGCCAAGCTTGC-3% SEQ ID NO: 2), 20 pmol reverse primer (5'-GAC CGGCGCT-CAGTTGGAATTCTAG-3', SEQ ID NO: 1) and 2.5 μl full-length gene (step 6) were used. The PCR product was purified using NucleoSpin Extract (Macherey-Nagel; elution volume of 50 μl for 150 μl PCR product).

(Step 8) PCR Product Digestion:

After universal base replacement, 40 μl of purified PCR product (step 7) was digested with 30 U EcoRI (New England Biolab) for 3 hours at 37° C. 20 U of AgeI (New England Biolab) was then added to the digest and the mixture was incubated for additional 3 hours at 37° C. The digested product was purified using NucleoSpin Extract (Macherey-Nagel; elution volume of 25 μl).

(Step 9) Ligation and Transformation:

The ligation of the digested PCR product (step 8) and pEGFP cloning vector (preparatory step 2) was performed at room temperature for 1 hour using T4 DNA ligase (Roche, Mannheim, Germany) and transformed into E. coli XL2 Blue (Stratagene, Amsterdam, Netherlands) cells. Competent cells were prepared by resuspending the cell pellet of a 50 ml culture (OD$_{578}$ 0.4-0.5) in 2 ml TSS buffer (10 g PEG 6000; 5 ml DMSO; 0.6 g MgSO$_4$; 100 ml LB). 5 μl ligation mixture was added to 200 μl cell aliquot followed by incubation in ice for 20 min, heat-shock s at 42° C. for 45 sec and additional chilling in ice for 2 min. After adding 0.8 ml of LB, the culture was shaken at 37° C. and 170 rpm for 1 hour. Cells were harvested by centrifugation at 3000 g, room temperature for 2 min. 900 μl of supernatant was discarded and cells were gently resuspended in the remaining 100 μl of supernatant. The cells were then plated on LB/Amp plate and incubated at 37° C. for overnight.

LITERATURE

Figure 1:
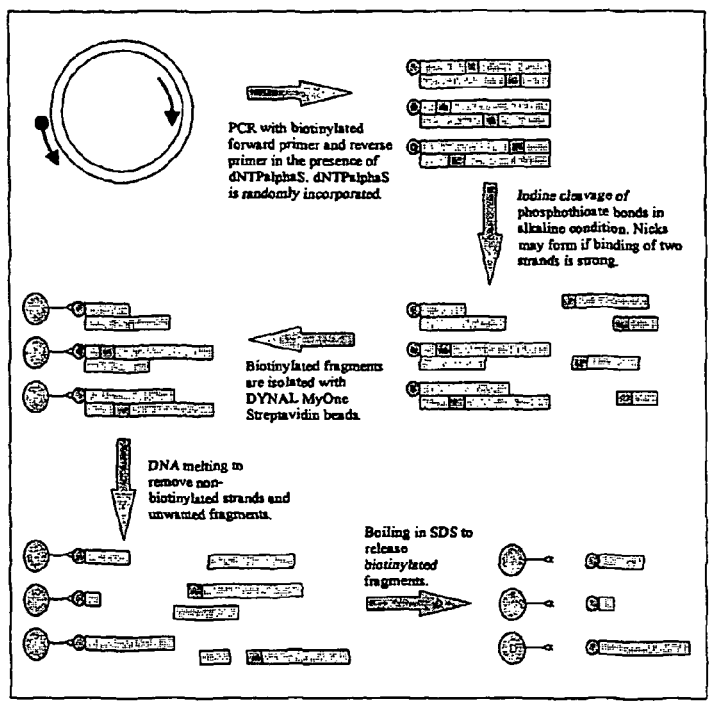
FIG. 1: a) Step (i): A random fragment size distribution is created b) Upper and middle gel picture: PCR product before (left lane) and after (right lane) iodine cleavage. Lower gel picture: DNA fragment size distribution after DNA melting and purification for different concentration of Sp-dATPαS (stated at the lower part of the lane).
Figure 1:
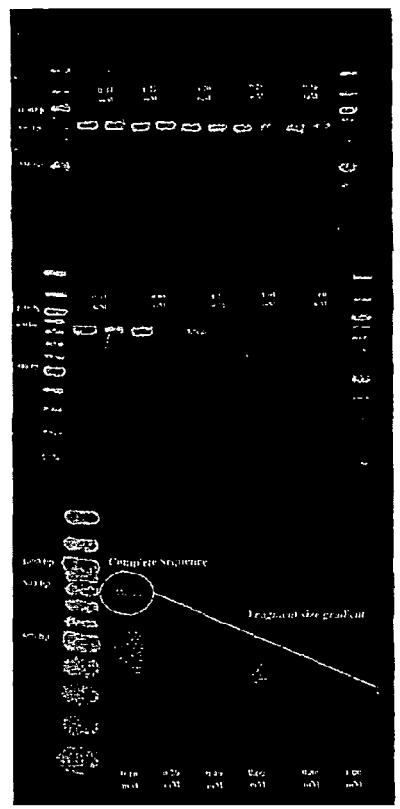
Figure 2:
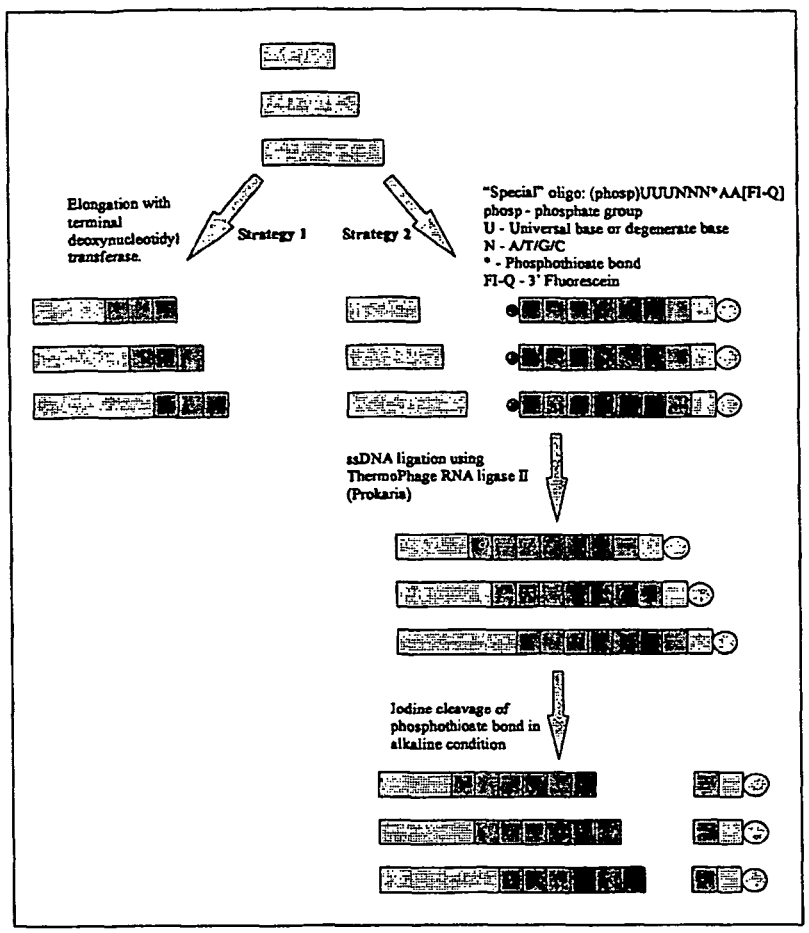
FIG. 2: a) Step (ii): DNA fragments elongated with universal or degenerate bases b) Lower left gel picture: PCR with primers elongated with different concentration of deoxyinosine at 3'-termini using terminal deoxynucleotidyl transferase. Lower right gel picture: PCR with primers elongated with different concentration of 5-nitroindole at 3'-termini using terminal deoxynucleotidyl transferase.
Figure 2:
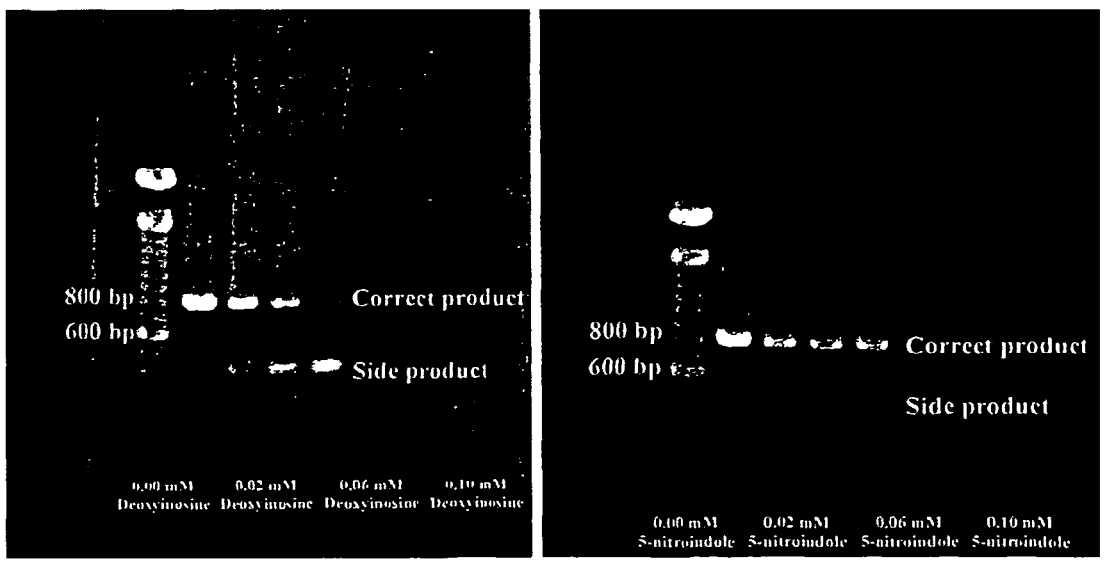
Figure 3:
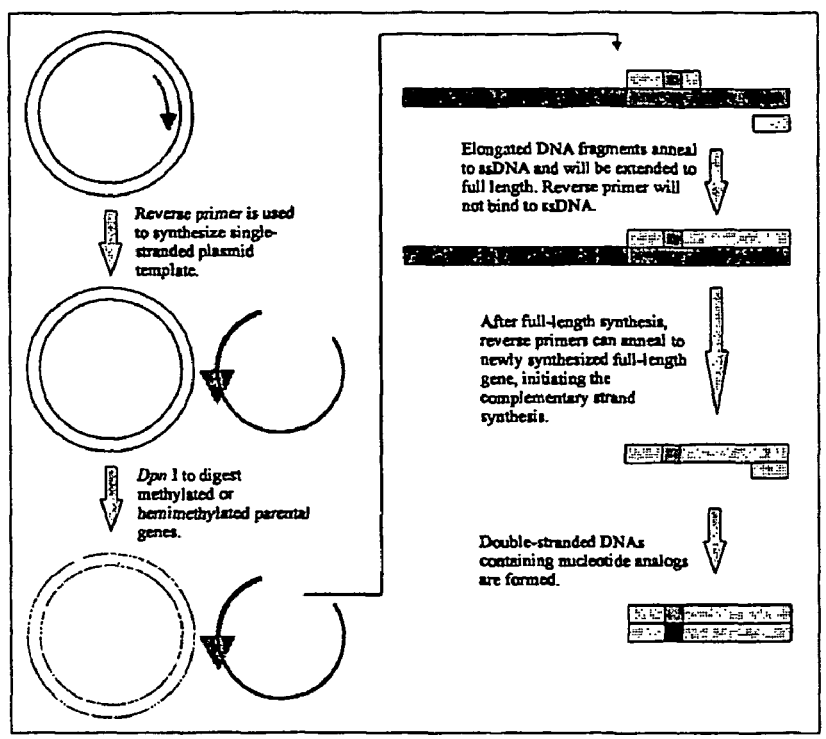
FIG. 3: Step (iii): Synthesis of full-length genes containing nucleotide analogs
Figure 4:
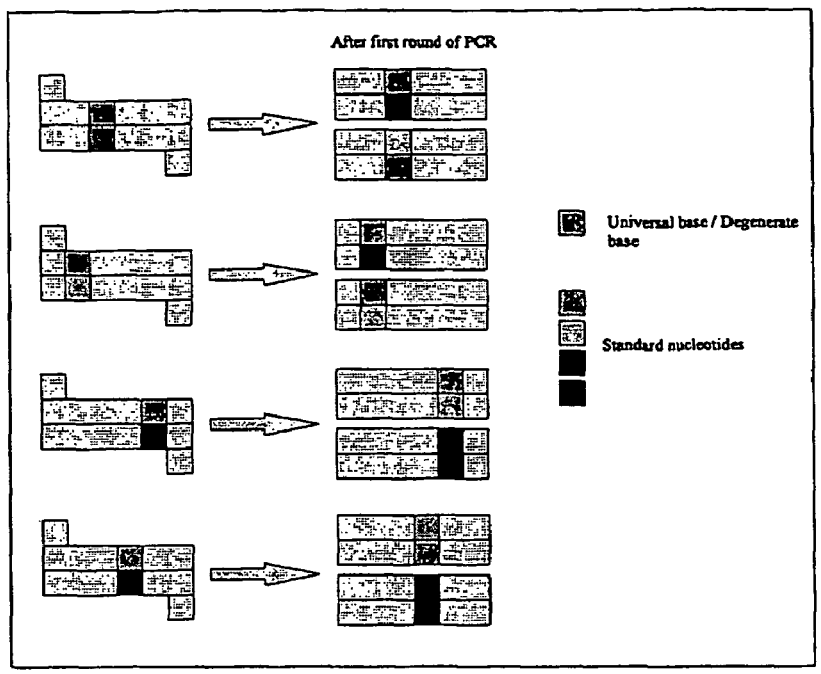
FIG. 4: Step (iv): Nucleotide analogs are replaced by standard nucleotides.
Figure 5:
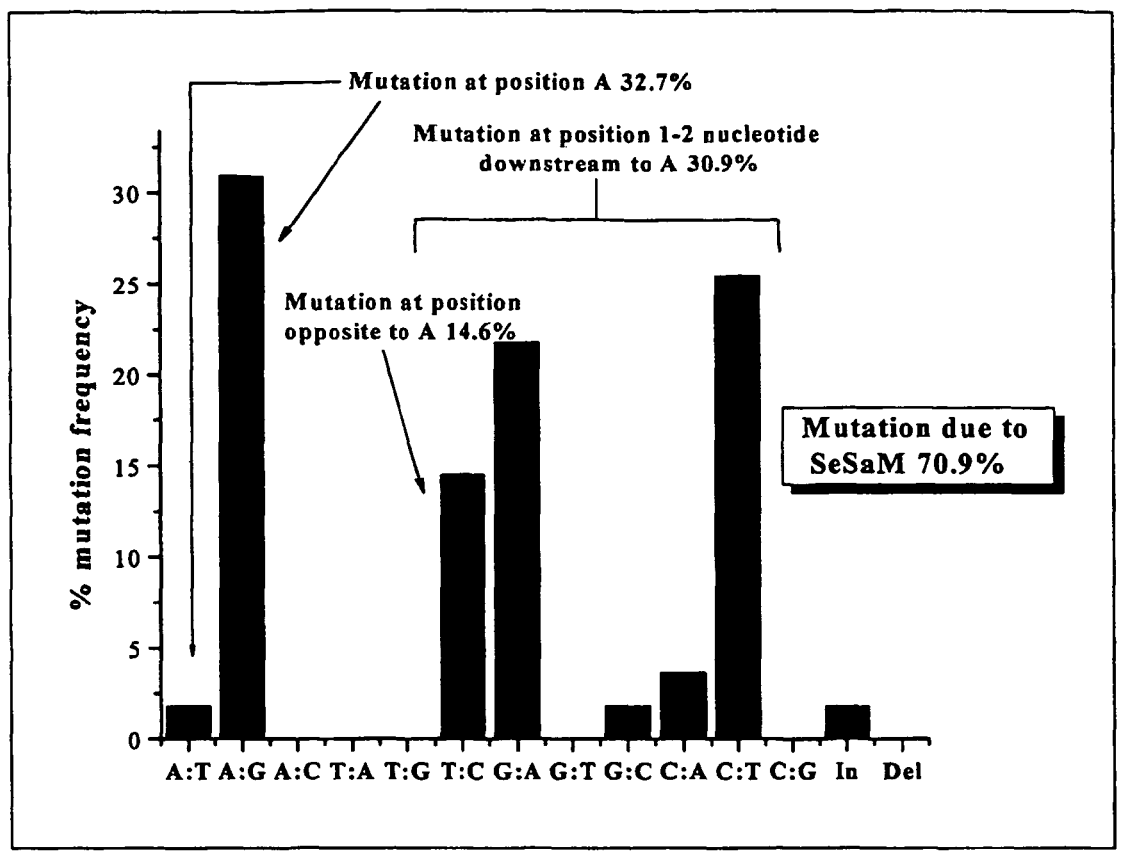
FIG. 5: Sequencing result of 100 randomly picked clones.
Figure 6:
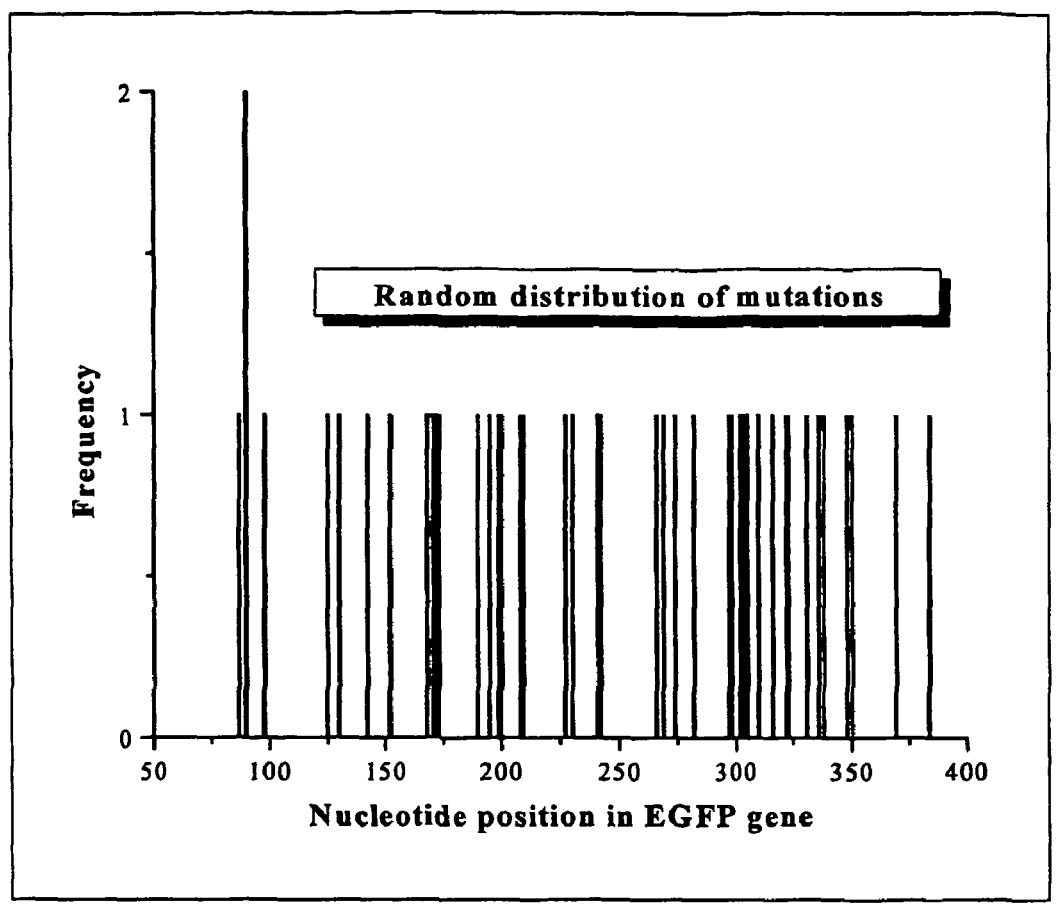
FIG. 6: Random distribution of mutations of 100 sequenced clones.

1. Arnold, F. H., Wintrode, P. L., Miyazaki, K. and Gershenson, A. (2001) *Trends Biochem. Sci.*, 26, 100-106.
2. Cadwell, R. C. and Joyce, G. F. (1994) *PCR Meth. App.*, 2, 136-140.
3. Lin-Goerke, J. L., Robbins, D. J. and Burczak, J. D. (1997) *Biotechniques*, 23, 409-412.
4. Cadwell, R. C. and Joyce, G. F. (1992) *PCR Meth. Appl.*, 2, 28-33.
5. Kuipers, O. P. (1996) *Meth. Mol. Biol.*, 57, 351-356.
6. Zaccolo, M., Williams, D. M., Brown, D. M. and Gherardi, E. (1996) *J. Mol. Biol.*, 255, 589-603.
7. Xu, H., Petersen, E. I., Petersen, S. B. and el-Gewely, M. R. (1999) *Biotechniques*, 27, 1102-1108.

The invention claimed is:

1. A process for the mutagenesis of a double-stranded polynucleotide sequence (master sequence) of n base-pairs having a (+)-strand and a complementary (−)-strand comprising the steps
   (i) creating a collection of single-stranded fragments of the (+)-strand of the master sequence wherein all members of the collection have the same 5'-terminus and have a deletion in the 3'-terminus such that the collection represents (+)-strands with a length of n−1, n−2, n−3, . . . nucleotides;
   (ii) introducing at least one universal or degenerate nucleotide at the 3'-terminus of the (+)-strands produced in step (i);
   (iii) elongating the (+)-strands produced in step (ii) to the full length of the master sequence using the (−)-strand or fragments thereof of the master sequence as a template strand for the elongation; and
   (iv) synthesizing a (−)-strand by using the (+)-strand produced in step (iii) as a template strand thereby effecting mutations in the (−)-strand at the positions of the previous universal or degenerate nucleotides compared to the master sequence.

2. The process of claim 1, wherein the collection of single-stranded fragments in step (i) is created by incorporating nucleotide analogs and subsequent cleavage in alkaline or acidic solution.

3. The process of claim 2, wherein the nucleotide analog is an alpha-phosphothioate nucleotide and oxidative cleavage is achieved by iodine at the phosphothioate bonds.

4. The process of claim 1, wherein step (ii) comprises elongating the collection of single-stranded fragments produced in step (i) with at least one universal or degenerate nucleotide by enzymatic or chemical methods.

5. The process of claim 4, wherein terminal deoxynucleotidyl transferases or DNA polymerases or DNA/RNA ligases are used for elongation.

6. The process of claim 1, wherein deoxyinosine, 3-nitropyrrole, 5-nitroindole or a nucleotide analog with promiscuous base pairing property is used as a universal nucleotide in step (ii).

7. The process of claim 1, wherein $N^6$-methoxy-2,6-diaminopurine (K), $N^6$-methoxy-aminopurine (Z), hydroxylaminopurine (HAP), 2'-deoxyribonucleoside triphosphate (dyTP), 6H,8H-3,4-dihydropyrimidol [4,5-c][1,2] oxazin-7-one (P), $N^4$-aminocytidine, $N^4$-hydroxy-2'-deoxycytidine, $N^4$-methoxy-2'-deoxycytidine, 8-oxodeoxy-guanosine triphosphate (8-oxo-G) or a nucleotide analog with promiscuous base pairing property is used as degenerate nucleotide in step (ii).

8. The process of claim 1, wherein an oligonucleotide of the general formula $$p(U)_n (N)_b {}^*(S)_c [\text{TERM}]$$

with p=5'-phosphate or hydroxy-group or any chemical group capable of forming diester bonds
U=universal or degenerate nucleotides
a=arbitrary integral number from 0 to 10000
N=mixture of four bases (A/T/G/C (standard nucleotides))
b=arbitrary integral number from 0 to 100
*=cleavable group such as phosphothioate bonds in phosphothioate nucleotides
S=standard nucleotide or nucleotide analog
c=arbitrary integral number from 0 to 100
[TERM]=a dye terminator or any group preventing elongation of the oligonucleotide, with the proviso that a+b>0,
is used in step (ii) to introduce the at least one universal or degenerate nucleotide to the collection of single-stranded fragments created in step (i).

9. The process of claim 8, wherein the oligonucleotide is designed in a way that
(a) stop codons and/or
(b) amino acids which disrupt secondary structures,
are avoided in the collection of the mutagenized polynucleotide sequences.

10. The process of claim 8, wherein the oligonucleotide is designed in a way that
(a) transition mutations or
(b) transversion mutations,
are effected in the collection of the mutagenized polynucleotide sequences.

11. The process of claim 8, wherein a DNA/RNA ligase is used for ligation of the oligonucleotides to the single-stranded fragments created in step (i), and wherein single-stranded fragments created in step (i) which are not ligated to the oligonucleotide are removed using an exonuclease.

12. The process of claim 1, wherein the elongation in step (iii) is effected by a PCR reaction.

13. The process of claim 1, wherein step (iii) comprises synthesizing a (−)-single stranded plasmid polynucleotide sequence from a double-stranded plasmid harboring the master sequence using a primer which anneals downstream of the (+)-strand of the master sequence, and annealing the (−)-single stranded-plasmid polynucleotide sequence with the (+)-strand produced in step (ii), and elongating the (+)-strand.

14. The process of claim 1, wherein step (iii) comprises synthesizing a (−)-single-stranded plasmid harboring the master sequence using a primer which anneals downstream of the (+)-strand of the master sequence in the presence of uracil and standard nucleotides and after elongating the (+)-strand produced in step (ii), digesting the uracil carrying (−)-single-stranded plasmid with uracil glycosylase.

15. The process of claim 1, wherein a PCR amplification is used after step (iii) in order to synthesize a (−)-strand complementary to the (+)-strand produced in step (iii), thereby effecting a double-stranded master sequence carrying mutations.

* * * * *

UNITED STATES PATENT AND TRADEMARK OFFICE
CERTIFICATE OF CORRECTION

PATENT NO.        : 7,790,374 B2                                    Page 1 of 1
APPLICATION NO.   : 10/573639
DATED             : September 7, 2010
INVENTOR(S)       : Ulrich Schwaneberg It is certified that error appears in the above-identified patent and that said Letters Patent is hereby corrected as shown below:

On the Cover Page, left column:

In item (73) Assignee: "BASF Aktiengesellschaft, Ludwigshafen (DE)" should read
-- SeSaM-Biotech GmbH, Bremen (DE); Jacobs University Bremen gGmbH, Bremen (DE) --

Signed and Sealed this
Twelfth Day of July, 2011

David J. Kappos
*Director of the United States Patent and Trademark Office*